United States Patent [19]

Hoegnelid et al.

[11] Patent Number: 5,480,420
[45] Date of Patent: Jan. 2, 1996

[54] RESORBABLE TEMPORARY MEDICAL ELECTRODE DEVICE

[75] Inventors: Kurt Hoegnelid, Vaesterhaninge, Sweden; Hans Thornander, Recloses, France; Martin Obel, Danderyd, Sweden

[73] Assignee: Siemens Elema AB, Solna, Sweden

[21] Appl. No.: 299,345

[22] Filed: Sep. 1, 1994

[30] Foreign Application Priority Data

Sep. 24, 1993 [SE] Sweden ................................ 9303120

[51] Int. Cl.⁶ ..................................................... A61N 1/04
[52] U.S. Cl. ............................................ 607/116; 128/642
[58] Field of Search ............................. 128/642; 607/116, 607/119, 120, 121, 122, 126, 129

[56] References Cited

U.S. PATENT DOCUMENTS 3,915,174  10/1975  Preston .
4,258,724  3/1981   Balat et al. .
4,644,960  2/1987   Johans ................................. 607/120
5,345,933  9/1994   Peterson et al. .

*Primary Examiner*—William E. Kamm
*Assistant Examiner*—Marianne Parker
*Attorney, Agent, or Firm*—Hill, Steadman & Simpson

[57] ABSTRACT

A temporarily implantable electrode device, intended for sensing electrical signals from living tissue, has an insulating sheath of resorbable material, and at least one non-toxic, liquid conductor contained inside the insulating sheath in order to form an electrical conductor which, via an electrode adapted for interaction with living tissue can sense and carry electrical signals from living tissue to a medical apparatus connected to the electrode device. The resorbable material ultimately dissolves completely into the body of the subject in whom the electrode device was temporarily implanted, and the non-toxic, liquid conductor simultaneously mixes with other fluids, making explantation of the electrode device unnecessary.

13 Claims, 2 Drawing Sheets

RESORBABLE TEMPORARY MEDICAL ELECTRODE DEVICE

BACKGROUND OF THE INVENTION

1. Field of the Invention

The present invention is directed to an electrode device intended to be at least partially implanted temporarily into living tissue.

2. Description of the Prior Art and Related Application

In general, medical electrode devices intended for implantation in a patient include an electrically insulating sheath, an electrical conductor contained in the insulating sheath, an electrode disposed on the insulating sheath, and in electrical contact with the conductor, and a contact disposed at proximal end of the insulating sheath and also in electrical contact with the conductor. The contact is adapted for electrical and mechanical connection to a medical apparatus which emits and/or receives electrical signals, which are carried by conductor. The electrode interacts with living tissue to either deliver a signal from the medical apparatus to the tissue, or to sense a signal from the living tissue and to supply it, via the conductor, to the medical apparatus.

An electrode device of this type is described in U.S. Pat. No. 3,915,174. This known electrode device can be implanted in a heart either temporarily or permanently in order to stimulate the heart and to sense electrical heart signals. The electrode device can be connected either to an extracorporeal apparatus, or to an implantable apparatus, such as a pacemaker.

The utilization of temporary electrode devices for sensing electrical signals in body tissue is very useful in conjunction with, for example, the diagnosis of illnesses and in determining the most appropriate treatment for a patient. When such determination could include, for example, an investigation of whether a patient should be provided with an implantable defibrillator.

For reception of usable values in the monitoring of electrical signals in living tissue, the electrode device must be connected to the tissue in a reliable manner. Many different ways are known to attach the electrode device to tissue. In general, these known fixing techniques employ either an active fixing means or a passive fixing means. When the electrode device is attached to the tissue it will, after only a relatively short period of time, become embedded in the tissue. As a result, the electrode device cannot be easily removed after the investigation has been completed. Because the electrode becomes firmly embedded in tissue, the tissue may be damaged when the electrode device is explanted. Explanting a temporary electrode device, moreover, requires surgery as a rule, thereby increasing the risk to the patient. A common recourse for minimizing trauma to tissue and risk to the patient is simply to leave the electrode device implanted in the patient. This solution, however, is not without risk, because the electrode device, if left in the body, may irritate and even damage other tissue.

In the case of purely mechanical implants, i.e., implants not involving the transmission of electrical signals, which are only needed temporarily in the body of a patient, resorbable materials are currently being used to a large degree. The resorbable material gradually dissolves in the body, ultimately disappearing completely, and is usually replaced by living tissue. The presence of an electrical conductor, however, is a problem in implants wherein electrical signals must be transmitted. No resorbable electrical conductors are currently known.

In co-pending U.S. application Ser. No. 08/226,337 ("Medical Electrode Device Having A Non-Gaseous Fluid Conductor," Hoegnelid et al., filed Apr. 12, 1994), an electrode device is disclosed wherein, instead of using a metallic conductor, a nongaseous fluid conductor is used in order to reduce the risk of conductor fracture and short-circuits between conductors. Various types of non-gaseous fluid conductors are described therein, one of which, for sensing signals from tissue, is a liquid conductor consisting of an electrolyte. The electrolyte may be sodium chloride and water, making it completely harmless to tissue.

SUMMARY OF THE INVENTION

It is an object of the present invention to provide a medical electrode device of the type having an insulating sheath containing an electrical conductor and having at least one electrode for interaction with living tissue, which is temporarily implantable in living tissue and which does not require explantation.

The above object is achieved in accordance with the principles of the present invention in an electrode device having an insulating sheath made of a resorbable material, and having an electrical conductor made of a non-toxic, electrically conductive liquid, preferably an electrolyte.

The insulating sheath in the electrode device constructed in accordance with the principles of the present invention will ultimately dissolve completely in the body, and the liquid conductor will mix with body fluids without causing any damage. The only part remaining in the body will be the electrode itself.

If the electrode is made with a small contact area for interaction with tissue, for example, one or a few square millimeters, the electrode does not have to be embedded into the tissue and can be permitted, for example, to follow the circulating blood when the insulating sheath dissolves.

The electrode is preferably disposed at a distal end of the insulating sheath, i.e., the end of the sheath opposite from the end which is intended to be connected to the medical apparatus. This embodiment facilitates the implantation procedure. In this embodiment, the electrode can be embedded into the tissue during implantation, and thus poses no risk to the tissue.

Alternatively, the electrode can be a membrane made of an ion-transporting material. In this embodiment, no metallic material would remain behind in the body, only a thin membrane embedded in the tissue. In some cases, however, it may still be preferable to employ electrodes consisting of a non-toxic, biocompatible metal, or of organic (carbon-based) material.

In a further embodiment of the invention, at least one additional electrical conductor is contained in the insulating sheath, electrically insulated from the first electrical conductor, the additional electrical conductor also consisting of a non-toxic electrically conductive liquid, preferably an electrolyte. At least one further electrode is arranged on the insulating sheath to transmit electrical signals to and from the further electrical conductor.

By increasing the number of liquid conductors and electrodes, a single electrode device can be used to sense a plurality of tissue regions simultaneously. For example, a plurality of measurement points around or in the heart could be sensed simultaneously. In a similar manner, several locations along a muscle or along a nerve path can be sensed for electrical signals simultaneously.

In this context, it is preferable for the further electrode to be a membrane made of an ion-transporting material. As in the case of the aforementioned electrode, however, there may be cases in which it is preferable to make the further electrode of a non-toxic biocompatible metal, or of an organic material.

As in the case of the initially described electrode, the further electrode can have such a small area, for example one or a few square millimeters, so that it does not have to be affixed to tissue, but can follow the circulating blood when the sheath dissolves.

In a further version of the invention, the ion-transporting material forming the electrode or the further electrode can also be resorbable.

DESCRIPTION OF THE PREFERRED EMBODIMENTS

Figure 1:
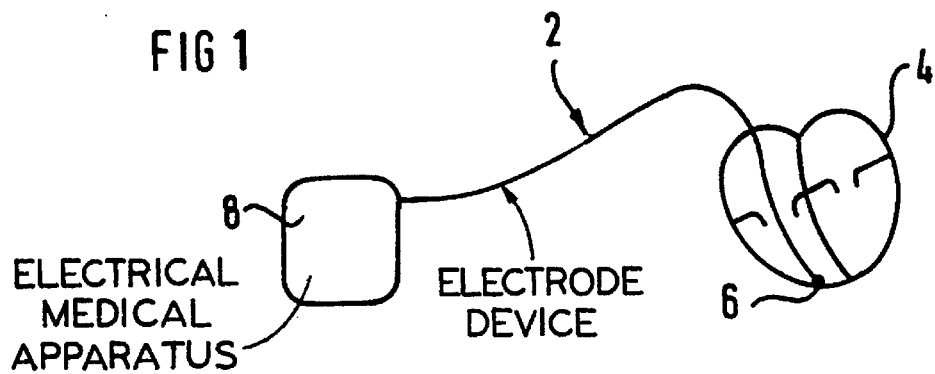
FIG. 1 schematically illustrates a first of an electrode device constructed in accordance with the principles of the present invention.

An electrode device 2 constructed in accordance with the principles of the present invention is shown in FIG. 1 intravenously introduced into a heart 4, and electrically connected to the heart 4 by means of a tip electrode 6 for sensing electrical signals in the heart 4. At its opposite end, the electrode device 2 is connected to an electrical medical apparatus 8 such as a monitor which acquires and stores the sensed heart signals. The electrical medical apparatus 8 can either be extracorporeal or implantable.

Figure 2:
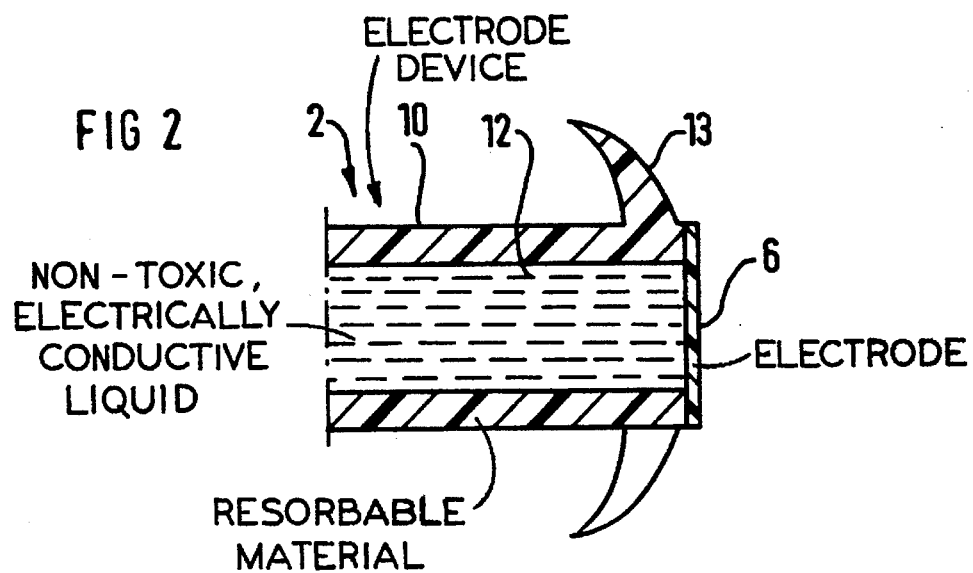
FIG. 2 is a sectional view showing a first embodiment of an electrode device constructed in accordance with the principles of the present invention.

The distal region of the electrode device 2 is shown in detail in FIG. 2, in cross section, in order to illustrate the design of the electrode device 2. The tip electrode 6 consists of a thin membrane of an ion-transporting material, for detecting signals from heart tissue. An insulating sheath 10 consists of resorbable material, and contains an electrical conductor formed by non-toxic electrically conductive liquid 12, such as an electrolyte. In order to affix the tip electrode 6 to the heart tissue, the insulating sheath 10 is provided with a pair of barb-like projections 13, which are affixed to the heart tissue upon implantation. The insulating sheath 10 as well as the projections 13 are made of a resorbable material. This means that the sheath 10 and the projections 13 will dissolve into the body after a time, and the electrolyte 12 will mix with other body fluids. If the ion-transporting material forming the electrode 6 is also made of a resorbable material, none of the implanted components will remain in the body after a time.

Figure 3:
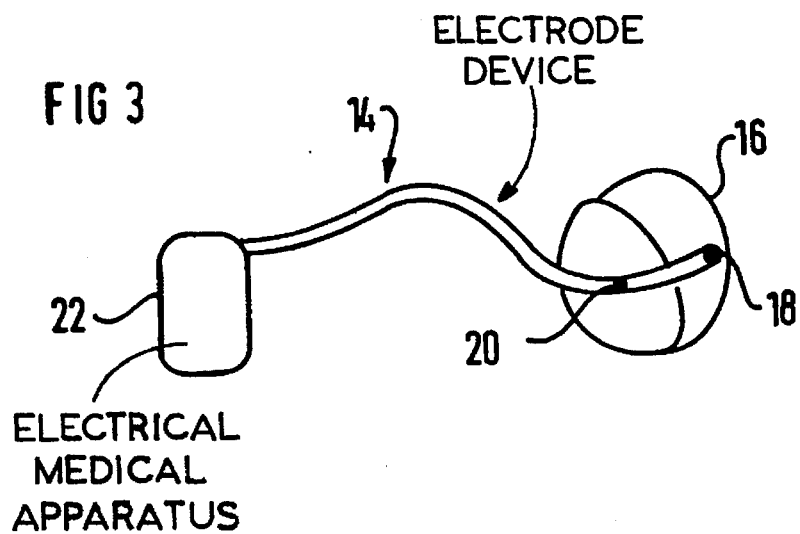
FIG. 3 schematically illustrates a second use of the electrode device constructed in accordance with the principles of the present invention.

Another electrode device 14 is shown in FIG. 3, connectable to the exterior of a heart 16 by a first electrode 18 and a second electrode 20 for sensing electrical signals the heart 16. The electrode device 14 is connected to an electrical medical apparatus 22 such as a monitor which detects and stores the sensed electrical signals in the same way as the apparatus 8 in FIG. 1.

Figure 4A:
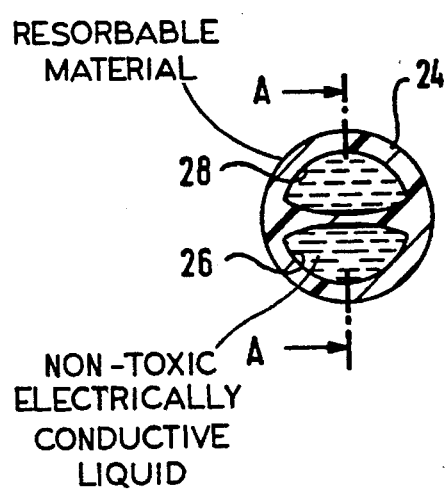
FIGS. 4a and 4b respectively show end and side sectional views of a second embodiment of an electrode device constructed in accordance with the principles of the present invention.
Figure 4B:
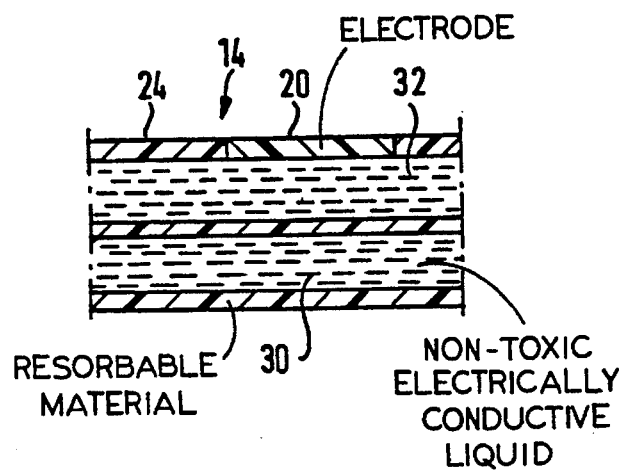

A first version of the electrode device 14 is shown in FIGS. 4a and 4b. The insulating sheath 24 has an interior partition which divides the electrode device 14 into a first channel 26 and a second channel 28. The first channel 26 is filled with a first non-toxic electrically conductive liquid 30, forming a first conductor, and the second channel 28 is filled with a second non-toxic electrically conductive liquid 32, forming a second conductor. The first and second non-toxic electrically conductive liquids 30 and 32 may both be formed by an electrolyte.

The first electrode 18 can be formed in the same manner as the electrode 6 shown in FIG. 2., i.e., as a thin membrane of an ion-transporting material, which is in contact with the first non-toxic electrically conductive liquid 30 in the first channel 26. The second electrode 20 may also be a thin membrane of an ion-transporting material, which may form a part of a wall of the second channel 28, and is accordingly in contact with the second non-toxic electrically conductive liquid 32, in order to detect signals from heart tissue and permit those signals to be transmitted to the apparatus 22. The distal end of the channel 28 is closed by resorbable material, so that the second non-toxic electrically conductive liquid 32 is not in contact with the first electrode 18.

Figure 5A:
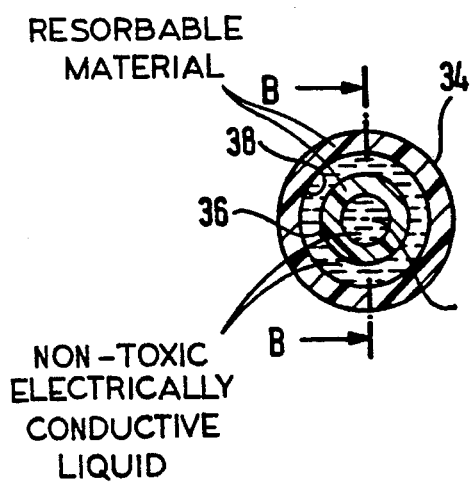
FIGS. 5a and 5b respectively show end and side sectional views of a third embodiment of an electrode device constructed in accordance with the principles of the present invention.
Figure 5B:
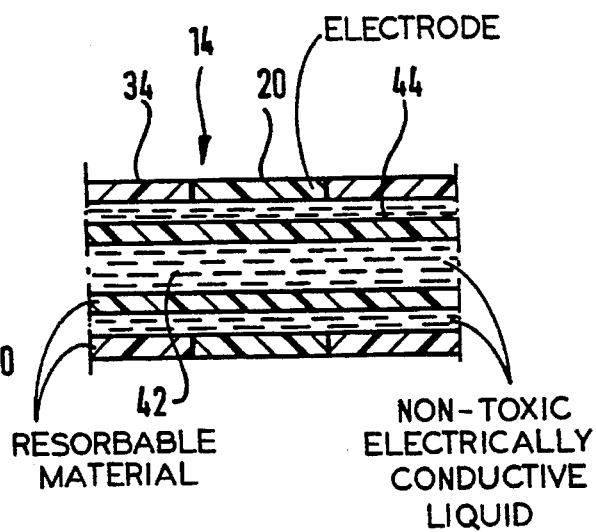

Another version of the electrode device 14 is shown in FIGS. 5a and 5b, in which an insulating sheath 34 encloses an insulating tube 36. This creates an annular channel between the insulating sheath 34 and the insulating tube 36. The insulating tube 36 has a channel 40 extending therethrough. Both the insulating sheath 34 and the insulating tube 36 consists of resorbable material. The channel 40 is filled with a first non-toxic electrically conductive liquid 42, forming a first conductor, and the annular channel 38 is filled with a second non-toxic electrically conductive liquid 44, forming a second conductor. Both the first and second non-toxic electrically conductive liquids 42 and 44 may be an electrolyte.

The second electrode 20 is a thin annular membrane formed of an ion-transporting material, which forms a part of the outer wall of the annular channel 38, and is thus in contact with the second non-toxic electrically conductive liquid 44 in order to transmit electrical signals from the heart 16 to the apparatus 22. If the membrane has only a very small area, such as a few square millimeters, it does not need to consist of resorbable material.

The insulating tube 36 terminates in an electrode similar to the electrode 6 shown in FIG. 1, and the insulating sheath 34 terminates short of this electrode so that the second non-toxic electrically conductive liquid 44 does not come into contact with that electrode.

The invention is not limited to the above-described embodiments but may, for example, contain an optional number of conductors each formed by a non-toxic electrically conductive liquid, such as an electrolyte, for sensing at different tissue points in a body. Combinations of the above-described embodiments are also possible.

An electrolyte is only one example of a non-toxic electrically conductive liquid which may form the conductor or conductors in the above embodiments. The electrodes can alternatively be made of non-toxic biocompatible metal, or organic materials.

Regardless of whether the apparatus 8 or the apparatus 22 is implantable, it can implement a number of measurement functions contributing information as to the state of health of the patient in whom the electrode device is implanted. For example, blood pressure and pH are useful parameters to be obtained in conjunction with recordings of the electrical signal of the heart, and improve the ability of the physician to make a correct diagnosis. In principle, the apparatus 8 or 33 can be equipped to measure all variables and parameters which are of interest to the physician, using various types of known sensors and measurement techniques. The recording sensors and signal transmitter affixed to the tissue can suitably be made of a resorbable material, whereas the sensors and transmitters not affixed to tissue, and which are easily removed without risk to the patient, can be in the form of conventional measurement sensors.

Although the above embodiments have been described in the context of measuring electrical heart signals, the same or similar electrode devices can be used for sensing electrical signals from other types of living tissue, such as muscles and nerves.

The electrode disclosed herein can be employed for temporary electrical stimulation of living tissue, such as muscle tissue, heart tissue and nerves. For such use, the electrical medical apparatus will be a stimulation pulse generator, instead of a monitor.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrode device for at least partial implantation temporarily into living tissue, comprising:
   an electrically insulating sheath consisting of resorbable material;
   an electrical conductor contained in said insulating sheath consisting of a non-toxic electrically conductive liquid; and
   an electrode carried by said insulating sheath and in electrical contact with said electrical conductor, and adapted for electrically interacting with living tissue.

2. An electrode device as claimed in claim 1 wherein said non-toxic electrically conductive liquid consists of an electrolyte.

3. An electrode device as claimed in claim 1 wherein said electrode has an area adapted for contact with said living tissue of a few square millimeters.

4. An electrode device as claimed in claim 1 wherein said insulating sheath has a distal end and wherein said electrode is disposed at said distal end of said insulating sheath.

5. An electrode device as claimed in claim 1 wherein said electrode consists of a membrane of an ion-transporting material.

6. An electrode device as claimed in claim 1 wherein said electrode consists of a non-toxic biocompatible metal.

7. An electrode device as claimed in claim 1 wherein said electrode is comprised of an organic material.

8. An electrode device for at least partial implantation temporarily into living tissue, comprising:
   an insulating sheath consisting of resorbable material having a plurality of separate channels therein;
   a plurality of electrical conductors respectively disposed in said channels, each electrical conductor consisting of a non-toxic electrically conductive liquid; and
   a plurality of electrodes carried by said insulating sheath and respectively in electrical contact with said plurality of electrical conductors, each electrode adapted for electrical interaction with living tissue.

9. An electrode device as claimed in claim 8 wherein at least one of said electrical conductors consists of an electrolyte.

10. An electrode device as claimed in claim 8 wherein at least one of said electrodes consists of a membrane of an ion-transporting material.

11. An electrode device as claimed in claim 8 wherein at least one of said electrodes consists of a membrane of a resorbable ion-transporting material.

12. An electrode device as claimed in claim 8 wherein at least one of said electrodes consists of a non-toxic biocompatible metal.

13. An electrode device as claimed in claim 8 wherein at least one of said electrodes consists of organic material.

* * * * *